United States Patent [19]
Zölss et al.

[11] 3,983,169
[45] Sept. 28, 1976

[54] PHENOXYPROPYLAMINE DERIVATIVES

[75] Inventors: Gerhard Zölss, Linz; Heribert Pittner, Gmund; Heimo Stormann-Menninger-Lerchenthal; Irmgard Lindner, both of Linz, all of Austria

[73] Assignee: Chemie Linz Aktiengesellschaft, Austria

[22] Filed: Dec. 17, 1974

[21] Appl. No.: 533,689

[30] Foreign Application Priority Data
Dec. 21, 1973 Austria .............................. 10718/73

[52] U.S. Cl. .................. 260/501.17; 260/247.5 R; 260/293.79; 260/326.5 J; 260/326.5 L; 260/326.85; 260/559 A; 260/570.7; 260/553 A; 260/465 E
[51] Int. Cl.² .................. C07C 87/52; C07C 111/00
[58] Field of Search .................. 260/553 A, 501.17

[56] References Cited
UNITED STATES PATENTS
3,852,339  12/1974  Krapcho .................. 260/553 A X FOREIGN PATENTS OR APPLICATIONS
261,582  5/1968  Austria
286,963  1/1971  Austria
2,100,323  1/1971  Germany Primary Examiner—Allen B. Curtis
Attorney, Agent, or Firm—Wenderoth, Lind & Ponack

[57] ABSTRACT

Phenoxypropylamine derivatives of the general formula:

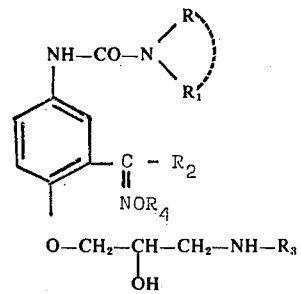

in which R is a hydrogen atom or a straight-chain or branched alkyl group containing up to 10 carbon atoms, $R_1$ is a hydrogen atom, a straight-chain or branched alkyl group containing up to 10 carbon atoms or a cyclopentyl, cyclohexyl, benzyl or phenyl group or R and $R_1$ taken together form a pentamethylene-(1,5), tetramethylene-(1,4), 2-azapentamethylene-(1,5), 3-azapentamethylene-(1,5) or 3-oxapentamethylene-(1,5)-group, $R_2$ is a hydrogen atom or an alkyl group containing up to 6 carbon atoms or a benzyl or phenyl group, $R_3$ is a branched alkyl group containing 3 to 6 carbon atoms, a cyanoalkyl group containing up to 6 carbon atoms or a cycloalkyl group containing 3 to 7 carbon atoms and $R_4$ is a hydrogen atom, an alkyl group containing up to 6 carbon atoms or a benzyl group, and the pharmaceutically-acceptable salts thereof having a cardioselective β-blocking action.

7 Claims, No Drawings

PHENOXYPROPYLAMINE DERIVATIVES

This invention relates to phenoxypropylamine derivatives and to a process for the preparation thereof. It is also concerned with pharmaceutical compositions containing such derivatives.

Substances with a blocking action on the β-receptors are assuming increasing importance in therapy for the treatment of various cardiac illnesses which may be explained in terms of cause or symptoms by an undesirably high content of catecholamines, originating from the body, in the circulation.

It has been possible to achieve a significant advance through the discovery of so-called cario-selective β-blocking agents, that is to say agents which predominantly display an action only on the β-receptors of the heart but have little action on β-receptors of other organs, since in this way it is possible to avoid adverse sideeffects such as, for example, a spastic effect on the respiratory tracts. However, of these selective agents hitherto only one substance, namely 1'-[4-acetaminophenoxy-(2'hydroxy-3'isopropylamino)]-propane, described in Austrian Patent Specification No. 261,582, has found acceptance in practice so that there continues to be a great need to find actually usable cardio-selective β-blocking agents. However, with many β-blocking agents an obstacle is an undesired cardiodepressive action which is frequently coupled with the β-blocking action.

The patent literature has also disclosed cardio-selective phenoxy-propylamine derivatives with a disubstituted ureido group in the p-position relative to the propylamine side chain (DOS 2,100,323) which may be substituted in the nucleus by hydrocarbon groups, ether groups, halogen atoms, trifluoromethyl groups or nitrile groups, and also cardio-selective β-blocking agents with a phenoxypropylamine structure which carry an oxime side-chain in the o-position to the propylamine side-chain and which optionally may be substituted in the nucleus, in any desired position, by one or more halogen atoms, nitro groups, aryl, alkanoylamino, alkyl or alkoxy groups, see Austrian Patent Specification No. 286,963.

Surprisingly, it has now been found that phenoxypropylamine derivatives which carry a ureido group in the p-position to the phenoxypropylamine chain and an oxime group in the o-position, and which have the general formula (1) as defined hereinafter, provide a strong β-blocking action with surprisingly good cardioselectivity and a reliable action when administered orally.

Accordingly the present invention provides a phenoxypropylamine derivative having the general formula:

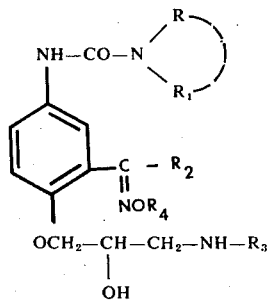

(I)

in which R is a hydrogen atom or a straight-chain or branched alkyl group containing up to 10 carbon atoms, $R_1$ is a hydrogen atom, a straight-chain or branched alkyl group containing up to 10 carbon atoms or a cyclopentyl, cyclohexyl, benzyl or phenyl group or R and $R_1$ taken together form a divalent, straight-chain or branched hydrocarbon group containing 4 to 7 carbon atoms in the main chain, it being possible for one or two of these carbon atoms to be replaced by oxygen, sulphur or nitrogen atoms, $R_2$ is a hydrogen atom or an alkyl group containing up to 6 carbon atoms or a benzyl or phenyl group, $R_3$ is a branched alkyl group containing 3 to 6 carbon atoms, a cyanoalkyl group containing up to 6 carbon atoms or a cycloalkyl group containing 3 - 7 carbon atoms and $R_4$ is a hydrogen atom, an alkyl group containing up to 6 carbon atoms or a benzyl group, and the pharmaceutically-acceptable acceptable salts thereof.

The activity of the compounds of formula (1) may be determined on awake dogs by the method of Dunlop and Shanks, Brit. J. Pharmacol. 32, 201–18, 1968. The cardioselective action may be recognised, for example, from the fact that according to the method of Shanks et al., Cardiologia Suppl. 11, 49, 11 (1966), carried out on drugged dogs, the increase in pulse rate occasioned by Isoprenalin is inhibited to a greater extent by prior administration of the above compounds than is the blood pressure lowering action of Isoprenalin. This action also may be seen in the case of rats from a blocking action on the Isoprenalin-conditioned increase in unesterified fatty acids ($\beta_1$-action) whilst hardly any effect on the lactate values and glucose values increased by Isoprenalin was found ($\beta_2$-action). Surprisingly, in spite of the high β-blocking action, the compounds of the formula (1) cause no lowering of the pulse rate, after peroral administration of the substances, when testing the pulse rate on awake dogs by a method based on that of Barrett and Carter, Brit. J. of Pharmacol. 40, 373-81 (1970): this indicates that the undesired and in part dangerous cardio-depressive action is absent in the case of the compounds of the formula (1). The toxicity of the compounds of the formula (1) in mice is the same as, or even lower than, that of the commercially available β-blocking agents.

The invention also provides a process for the preparation of a compound of the formula (1) herein, which comprises reacting a 2-acyl-phenoxpropylamine derivative of the general formula:

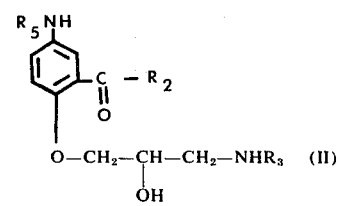

in which $R_5$ is a hydrogen atom or the

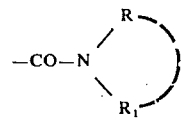

group, and R, R₁, R₂ and R₃ are as defined in formula (1) above, or a salt thereof with hydroxylamine or a derivative thereof of the general formula:

NH₂—O—R₄            (III)

in which R₄ is as defined in formula (1) above, or with a salt thereof and, when R₅ is a hydrogen atom the ureido group is introduced by reaction with a carbamic acid derivative of the general formula:

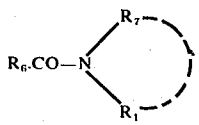

(IV)

in which R₆ is a halogen atom and R₇ has the same meaning as R, or R₆ and R₇ together form a further bond between the carbon and nitrogen atoms and isolating the resulting compound of the formula (1) as the free base or as a salt thereof.

The reaction is preferably carried out at room temperature in a polar solvent, for example a mixture of an aliphatic alcohol such as methanol or ethanol with water, or in a secondary or tertiary amine such as, for example, pyridine. The hydroxylamine or derivative thereof is preferably employed in excess. If a salt of a compound of the formula (III) is used as the starting material, this being preferred, a suitable method is to add this salt as an aqueous solution to the compound of the formula (11). The compound of the formula (1) is then obtained as the salt, unless an amine has been used as the solvent, and may be isolated as the salt or, after conversion, as the free base.

If both the compound of the formula (11) and the compound of the formula (III) are employed as salts it is advisable to carry out the reaction in a medium which buffers the acid liberated, which originates from the hydroxylamine salt of the formula (III).

It is immaterial, with regard to the reaction, whether R₅ in the formula (11) is a hydrogen atom or the

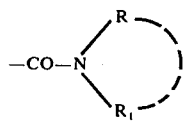

group. If R₅ is a hydrogen atom, the ureido group must subsequently be produced. This is achieved by reaction of the oxime, or an ether thereof of the general formula (V):

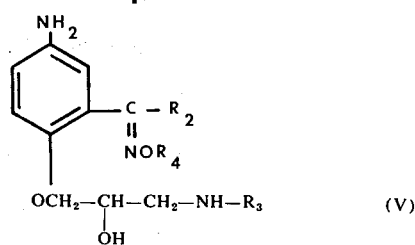

(V)

which is obtained as an intermediate compound and in which R₃ and R₄ are as defined in formula (1), with a carbamic acid derivative of the formula (1V). If a carbamic acid halide of the formula (1V) is used, the reaction is suitably carried out in the presence of an acid acceptor, for example in pyridine, as the solvent.

The compounds of the formula (11), in which R₂ and R₅ are not hydrogen atoms, which are used as the starting material for the process according to the present invention, are new and are described and claimed in Application No. 533,688 filed Dec. 17, 1974. They may be obtained by reaction of 3-acyl-4-hydroxyaniline with an appropriately substituted carbamic acid halide or isocyanate to give the urea derivative, after which the propanolamine side chain is introduced by reaction with epichlorohydrin and an appropriate amine. If a starting compound of the formula (11), in which R₂ is not a hydrogen atom and R₅ is a hydrogen atom is used, then this easily may be prepared from 3-acyl-4-hydroxy-acetanilide by reaction with epichlorohydrin and the appropriate amine (introduction of the propanolamine side chain) followed by acid saponification of the acid amide group. If a compound wherein R and R₁ are hydrogen atoms is being prepared, the reaction to give the ureido group is carried out with potassium cyanate. To prepare compounds which are only monosubstituted by a methyl or ethyl group at the urea group the method followed, because of the difficulty of obtaining the corresponding isocyanate, is to prepare the 3-acyl-4-benzyloxy-phenylisocyanate starting from a 3-acyl-4-hydroxyacetanilide, via the corresponding O-benzyl ether; the phenylisocyanate may be converted to the corresponding compound of the formula (11) after reaction with the lower alkylamine, followed by reductive elimination of the benzyl group.

A suitable method of preparing a compound of the formula (11), in which R₂ is a hydrogen atom, is to start from 5-nitro-salicylaldehyde, protect the aldehyde group by acetylisation, reduce the compound to the corresponding aminoaldehyde-acetal, react this with the desired carbamic acid derivative to give the urea, then introduce the aminopropoxy group and thereafter liberate the aldehyde group.

The compound of the formula (1) may be isolated in a customary manner. If it is present in the reaction mixture as a salt, it is advisable to liberate the base by rendering the mixture alkaline and to isolate the base as such or by extraction with an organic solvent. The base then may be converted to a salt thereof.

The compounds of the formula (1) have an asymmetrical carbon atom. They therefore exist as the racemate and as optically active forms. The separation of the racemate into the optically active forms is achieved in the usual manner, for example by forming the diastereomeric salts with optically active acids, for example tartaric acid or camphorsulphonic acid.

Among the compounds of the formula (1), those compounds in which R is a hydrogen atom or a straight-chain or branched alkyl group containing up to 6, preferably up to 4, carbon atoms display a particularly advantageous action. For compounds with a particularly advantageous action, $R_1$ is a hydrogen atom, an optionally branched alkyl group containing up to 6, preferably up to 4, carbon atoms, a benzyl group or a phenyl group. Compounds in which R and $R_1$ together with the terminal nitrogen atom of the ureido group represent a pyrrolidino, diazolidino, for example imidazolidino, thiazolidino, oxazolidino, piperidino, morpholino, tetrahydrodiazino, for example, tetrahydropyrimidino, tetrahydrothiazino or homopiperazino radical also possess a favourable action. The pyrrolidino, piperidino and morpholino groups are preferred in this respect.

Particularly favourable properties are exhibited, as a rule, by compounds in which each of R and $R_1$, which may be the same or different, is a hydrogen atom or an alkyl group containing 1 to 6, preferably 1 to 4, carbon atoms, or both groups together form a tetramethylene, pentamethylene or 3-oxapentamethylene group, $R_2$ is a hydrogen atom or a lower alkyl group containing 1 to 5 carbon atoms, $R_3$ is a tertiary butyl group or isopropyl group and $R_4$ is a hydrogen atom, an alkyl group containing 1 to 4 carbon atoms or a benzyl group.

The present invention further provides a pharmaceutical composition comprising, as the active ingredient, one or more compounds of the formula (1) herein, or a pharmaceutically-acceptable salt thereof, in admixture with one or more excipients or diluents.

The compounds of the formula (1) may be used, in the said compositions, either as the free base or as a pharmaceutically-acceptable salt. Examples of such pharmaceutically-acceptable salts are the hydrohalides, especially the hydrochlorides and hydrobromides, and also the sulphates, phosphates, acetates, fumarates, succinates, cyclohexylsulphamates, tartrates and citrates. These salts may be prepared, for example, by reacting the free base with an equivalent amount of the appropriate acid.

The compositions may be administered orally, rectally or parenterally. For this purpose, the compounds of the formula (1) are mixed with the customary pharmaceutically-acceptable excipients, the nature of the excipient depending on the type of administration. They may be made up into tablets or dragees in the usual manner. The active compounds themselves, optionally together with a pharmaceutically acceptable solvent, may be filled into capsules. Pharmaceutically-acceptable soluble salts which are capable of forming stable solutions may be made up into injectable solutions. The salts required for this purpose may be obtained in a simple manner from the corresponding bases of the formula (1) by reaction with the equivalent amount of acid. Both bases and salts may be converted to suppositories in the usual manner.

The individual dose for humans is preferably 100 mg in the case of peroral administration and correspondingly lower in the case of intravenous administration.

The following may be mentioned as examples of particularly preferred compounds: N-[3-(1'-hydroxyimino)-ethyl-4-(3'-tert.-butylamino-2'hydroxy)-propoxyl]-phenyl-n'-dimethylurea and the corresponding 3'-isopropylamino or secondary butylamino compound, N-[3-(1'-hydroxyimino)-ethyl-4-(3'-tert.-butylamino-2'-hydroxy)-propoxyl]-phenyl-N'-diethylurea, N-[3-(1'hydroxyimino)-ethyl-4-(3'-tert.-butylamino-2'-hydroxy)-propoxy]-phenyl-N'-tetramethylene-(1,4)-urea, N-[3-(1'-hydroxyimino)-ethyl-4-(3'-tert.-butylamino-2' hydroxy)-propoxy]-phenyl-N'-methylurea, N-[3-(1'-hydroxyimino)-ethyl-4-(3'-tert.-butylamino-2'-hydroxy)-propoxy]-phenyl-N'-dipropylurea, N-[3-(1'-hydroxyimino)-ethyl-4-(3'-tert.-butylamino-2'-hydroxy)-propoxy]-phenyl-N'-n-butylurea, N-[3-(1'hydroxyimino)-ethyl-4-(3'-tert.-butylamino-2'-hydroxy)-propoxy]-phenyl-N'-tert.-butylurea, N-[3-(1'hydroxyimino)-ethyl-4-(3'-tert.-butylamino-2'-hydroxy)-propoxy]-phenylurea, N-{3-(1'-hydroxyimino)-ethyl-4-[3'-(2''-hydroxymethyl-propyl(2'')-amino)-2'-hydroxy]-propoxy}-phenyl-N'-dimethylurea, N-[3-(1'-butoxyimino)ethyl-4-(3'-tert.-butylamino-2'-hydroxy)-propoxy]-phenyl-N'-dimethylurea, N-[3-(1'-hydroxyimino)-ethyl-4-(3'-tert.-butylamino-2'hydroxy)-propoxy]-phenyl-N'-sec.-butylurea, N-[3-(1'hydroxyimino)-ethyl-4-(3'-tert.-butylamino-2'-hydroxy)-propoxy]-phenyl-N'-methyl-N'-butylurea, N-[3-(1'-benzyloximino)-ethyl-4-(3'-tert.-butylamino-2'-hydroxy)-propoxy]-phenyl-N'-dimethylurea, N-[3-(hydroxyimino)-methyl-4-(3'-tert.-butylamino-2'-hydroxy)-propoxy]-phenyl-N'-dimethylurea, N-[3-(hydroxyimino)-methyl-4-(3'-tert.-butylamino-2'-hydroxy)-propoxy]-phenyl-N'-diethylurea, N-[3-(1'-hydroxyimino)-ethyl-4-(3'-tert.-butylamino-2'-hydroxy)-propoxy]-phenyl-N'dipropylurea and N-[3-(1'-hydroxyimino)-ethyl-4-(3'-tert.-butylamino-2'-hydroxy)-propoxy]-phenyl-N'phenylurea.

The following Examples illustrate the invention, and the manner in which it may be performed.

EXAMPLE 1

44.8 g. of hydroxylamine hydrochloride is dissolved in 90 ml of water, a solution of 75.5 g of N-[3-acetyl-4-(3'-tert.-butylamino-2'-hydroxy)-propoxy]-phenyl-N'-dimethylurea in 750 ml of methanol is added and the mixture is left to stand for 26 hours at room temperature. The solvent is distilled off in vacuo, the residue is taken up in 200 ml. of water, the mixture is rendered alkaline with 162 ml. of 4 N NaOH and seeded and the base which precipitates is filtered off, washed with water and dried over $P_2O_5$.

Yield of N-[3-(1'-hydroxyimino)-ethyl-4-(3'-tert.-butylamino- 2'-hydroxy)-propoxy]-phenyl-N'-dimethylurea: 76.0 g, representing 96.6% of theory. Melting point: 183° – 187° C 66.0 g. of the N-[3-(1'-hydroxyimino)-ethyl-4-(3'-tert.-butylamino-2'-hydroxy)-propoxy]-phenyl-N'-dimethylurea thus obtained is suspended in 500 ml. of hot ethanol, a solution of 10.5 g. of fumaric acid on 250 ml. of ethanol is added, followed by 150 ml. of water, the mixture is filtered and the filtrate is concentrated in vacuo to about 200 ml. 1,000 ml. of acetone is slowly added to the residue and the crystals which precipitate are filtered off, washed with acetone and ether and dried in vacuo at 80°C.

Yield of fumarate 76.2 g. representing 99.6% of theory. Melting point: 210° to 212°C.

The melting point of the hydrochloride obtained from the base in the usual manner is 208° to 211°C.

The N-[3-acetyl-4-(3'-tert.-butylamino-2'-hydroxy)-propoxy]-phenyl-N'-dimethylurea used as the starting material is obtained as follows:

3-Acetyl-4-hydroxy-aniline, in solution in pyridine, is reacted with dimethylcarbamoyl chloride at room temperature to give N-(3-acetyl-4-hydroxy)-phenyl-N'-dimethylurea, which after evaporating the pyridine, taking up the residue in chloroform and evaporating the latter, is obtained in a crystalline form. Melting point: 160° to 162°C. After reaction of the product, in alkaline aqueous solution, with epichlorohydrin, N-[3-acetyl-4-(2',3'-epoxy)-propoxy]-phenyl-N'-dimethylurea (melting point: 98° to 102°C) is obtained, and this, in turn, is reacted with excess tert.butylamine in aqueous solution at room temperature to give N-[3-acetyl-4-(3'-tert.-butylamino-2'-hydroxy)-propoxy]-phenyl-N'dimethylurea of melting point: 120° to 122°C.

EXAMPLE 2

3.8 g. of N-[3-acetyl-4-(3'-tert.-butylamino-2'-hydroxy)-propoxy]-phenyl-N'-diethylurea of melting point: 105° to 109°C is dissolved in 40 ml. of methanol, a solution of 2.1 g. of hydroxylamine hydrochloride in water is added and the mixture is left to react for 20 hours at room temperature. The methanol is distilled off in vacuo, 10 ml. of water is added to the residue, the mixture is rendered alkaline with 7.5 ml. of 4 N NaOH, the base which separates out is extracted with ethyl acetate, the organic phase is dried with $Na_2SO_4$ and the solvent is distilled off in vacuo. The residue crystallises after trituration with acetone. Yield of N-[3-(1'-hydroxyimino)-ethyl-4-(3'-tert.-butylamino-2'-hydroxy)-propoxy]-phenyl-N'-diethylurea 3.2 g, representing 81.0% of theory. Melting point: 148° to 152°C.

The fumarate may be prepared from the base by addition of the calculated amount of fumaric acid (in ethanol). Melting point: 209° to 212°C.

The following compounds may be obtained in an analogous manner to Examples 1 and 2.

3. N-[3-(1'-hydroxyimino)-ethyl-4-(3'-tert.-butylamino-2'-hydroxy)-propoxy]-phenyl-N'-tetramethylene-(1,4)-urea, melting point: 185° to 188°C., from N-[3-acetyl-4-(3'-tert.-butylamino-2'-hydroxy)-propoxy]-phenyl-N'-tetramethylene-(1,4)-urea of melting point: 123° to 128°C.

4. N-[3-(1'-hydroxyimino)-ethyl-4-(3'-tert.-butylamino-2'-hydroxy)-propoxy]-phenyl-N'-pentamethylene-(1,5)-urea, melting point of the fumarate: 170° to 173°C., from N-[3-acetyl-4-(3'-tert.-butylamino-2'-hydroxy)-propoxy]-phenyl-N'-pentamethylene-(1,5)-urea of melting point: 131° to 134°C.

5. N-[3-(1'-hydroxyimino)-ethyl-4-(3'-isopropylamino-2'-hydroxy)-propoxy]-phenyl-N'-dimethylurea, melting point of the fumarate: 175° to 178°C. from N-[3-acetyl-4-(3'-isopropylamino-2'-hydroxy)-propoxy]-phenyl-N'-dimethylurea, melting point: 103° to 107°C.

6. N-[3(1'-hydroxyimino)-ethyl-4-(3'-tert.-butylamino-2'-hydroxy)-propoxy]-phenylurea, melting point of the fumarate: 217° to 220°C. from N-[3-acetyl-4-(3'-tert.-butylamino-2'-hydroxy)-propoxy]-phenylurea, melting point: 158° to 161°C., prepared by reaction of 3-acetyl-4-hydroxyaniline with potassium cyanate.

7. N-[3-(1'-hydroxyimino)-ethyl-4-(3'-tert.-butylamino-2'-hydroxy)-propoxy]-phenyl-N'-methylurea, melting point: 104° to 106°C from N[3-acetyl-4-(3'-tert.-butylamino-2'-hydroxy)-propoxy]-phenyl-N'-methylurea, melting point: 132° to 134°C., obtained via 3-acetyl-4-benzyloxy-phenyliso-cyanate of melting point: 45° to 47°C, boiling point at 0.3 mm. = 171° to 172°C.

8. N-[3-(1'-hydroxyimino)-ethyl-4-(3'-tert.-butylamino-2'-hydroxy)-propoxy]-phenyl-N'-ethylurea, melting point: 108° to 110°C, from N-[3-acetyl-4-(3'-tert.-butylamino-2'-hydroxy)-propoxy]-phenyl-N'-ethylurea, melting point: 131° to 133°C., obtained via 3-acetyl-4-benzyloxy-phenylisocyanate.

9. N-[3-(1'-hydroxyimino)-ethyl-4-(3'-sec.-butylamino-2'-hydroxy)-propoxy]-phenyl-N'-dimethylurea, melting point of the fumarate: 192° to 195°C. (with decomposition), from oily N-[3-acetyl-4-(3'-sec.-butylamino-2'-hydroxy)-propoxy]-phenyl-N'-dimethylurea.

10. N-{3-(1'-hydroxyimino-ethyl-4-[3'-(2''-hydroxymethyl-propyl-(2'')-amino)-2'-hydroxy]-propoxy}-phenyl-N'-dimethylurea, melting point: 174° to 176°C., from oily N-{3-acetyl-4-[3'-(2''-hydroxymethyl-propyl(2'')-amino)-2'-hydroxy]-propoxy}-phenyl-N'-dimethylurea.

11. N-[3-(1'-Butoxyimino)-ethyl-4-(3'-tert.-butylamino-2'-hydroxy)-propoxy]-phenyl-N'-dimethylurea, melting point of the fumarate: 163° to 166°C., from N-[3-acetyl-4-(3'-tert.-butylamino-2'-hydroxy)-propoxy]-phenyl-N'-dimethylurea and O-butylhydroxylamine hydrochloride.

12. N-[3-(1'-Hydroxyimino)-ethyl-4-(3'-tert.-butylamino-2'-hydroxy)-propoxy]-phenyl-N'-dipropylurea, melting point of the fumarate: 163° to 166°C, from N-[3-acetyl-4-(3'-tert.-butylamino-2'-hydroxy)propoxy]-phenyl-N'-dipropylurea, melting point: 83° to 86°C.

13. N-[3-(1'-hydroxyimino)-ethyl-4-(3'-tert.-butylamino-2'-hydroxy)-propoxy]-phenyl-N'-sec.-butylurea, melting point of the fumarate: 225° to 228°C, from N-[3-acetyl-4-(3'-tert.-butylamino-2'-hydroxy)-propoxy]-phenyl-N'-sec.-butylurea.

14. N-[3-(1'-hydroxyimino)-ethyl-4-(3'-tert.-butylamino-2'-hydroxy)-propoxy]-phenyl-N'-butylurea, melting point: 93° to 95°C, from N-[3-acetyl-4-(3'-tert.-butylamino-2'-hydroxy)-propoxy]-phenyl-N'-butylurea, melting pont: 125° to 129°C.

15. N-[3-(1'-hydroxyimino)-ethyl-4-(3'-tert.-butylamino-2'-hydroxy)-propoxy]-phenyl-N'-tert.-butylurea, melting point of the fumarate: 220° to 225°C, from N[3-acetyl-4-(3'-tert.-butylamino-2'-hydroxy)-propoxy]-phenyl-N'-tert.-butylurea, melting point: 122° to 125°C.

16. N-[3-(1'-hydroxyimino)-ethyl-4-(3'-tert.-butylamino-2'-hydroxy)-propoxy]-phenyl-N'-dibutylurea, melting point of the fumarate: 171° to 174°C, from N-[3-acetyl-4-(3'-tert.-butylamino-2'-hydroxy)-propoxy]-phenyl-N'dibutylurea, melting point: 81° to 82°C.

17. N-[3-(1'-Hydroxyimino)-ethyl-4-(3'-tert.-butylamino-2'-hydroxy)-propoxy]-phenyl-N'-isopropylurea, melting point: 189° to 191°C, from N-[3-acetyl-4-(3'-tert.-butylamino-2'-hydroxy)-propoxy]-phenyl-N'-isopropylurea, melting point: 87° to 90°C.

18. N-[3-(1'-Methoxyimino)-ethyl-4-(3'-tert.-butylamino-2'-hydroxy)-propoxy]-phenyl-N'-dimethylurea, melting point of the fumarate: 163° to 167°C.

19. N-[3-(1'-Hydroxyimino)-ethyl-4-(3'-tert.-butylamino-2' hydroxy)-propoxy]-phenyl-N'-methyl-N'-isopropylurea, melting point: 145° to 148°C.

20. N-[3-(1'-Hydroxyimino)-ethyl-4-(3'-tert.-butylamino-2'-hydroxy)-propoxy]-phenyl-N'-methyl-N'-butylurea, melting point of the fumarate: 137° to 139°C.

21. N-[3-(1'-Hydroxyimino)-ethyl-4-(3'-tert.-butylamino-2'-hydroxy)-propoxy]-phenyl-N'methyl-N'-ethylurea, melting point of the fumarate: 212° to 216°C.

22. N-[3-(1'-Hydroxyimino)-ethyl-4-(3'-isopropylamino-2'-hydroxy)-propoxy]-phenyl-N'-diethylurea, melting point: 127° to 128°C.

23. N-[3-(1'-Benzyloxyimino-ethyl-4-(3'-tert.-butylamino-2'-hydroxy)-propoxy]-phenyl-N'dimethylurea, melting point of the fumarate: 164° to 167°C.

24. N-[3-(1'-Hydroxyimino)-methyl-4-(3'-tert.-butylamino-2'-hydroxy)-propoxy]-phenyl-N'-dimethylurea, melting point: 169° to 172°C.

25. N-[3-(1'-Hydroxyimino)-methyl-4-(3'-tert.-butylamino-2'-hydroxy)-propoxy]-phenyl-N'-diethylurea, melting point: 158° to 161°C.

26. N-[3-(1'-Hydroxyimino)-propyl-4-(3'-tert.-butylamino-2'-hydroxy)-propoxy]-phenyl-N'-diethylurea, melting point of the fumarate: 210° to 212°C.

27. N-[3-(1'-Hydroxyimino)-ethyl-4-(3'-tert.-butylamino-2'-hydroxy)-propoxy]-phenyl-n'-dipropylurea, melting point of the fumarate: 205° to 206°C.

28. N-[3-(1'-Hydroxyimino)-butyl-4-(3'-tert.-butylamino-2'-hydroxy)-propoxy]-phenyl-N'diethylurea, melting point of the fumarate: 178° to 180°C.

29. N-[3-(1'-Hydroxyimino)-propyl-4-(3'-tert.-butylamino-2'-hydroxy)-propoxy]-phenyl-N'-pentamethylene-(1,5)-urea, melting point of the fumarate: 156° to 158°C.

30. N-[3-(1'-Hydroxyimino)-propyl-4-(3'-tert.-butylamino-2'-hydroxy)-propoxy]-phenyl-N'-dimethylurea, melting point: 86° to 88°C.

31. N-[3-(1'-Hydroxyimino)-butyl-4-(3'-tert.-butylamino-2'-hydroxy)-propoxy]-phenyl-N'-pentamethylene-(1,5)-urea, melting point of the fumarate: 148° to 150°C.

32. N-[3-(1'-Hydroxyimino)-ethyl-4(3'-tert.-butylamino-2'-hydroxy)-propoxy]-phenyl-N'-phenylurea, melting point: 105° to 108°C.

33. N-[3-(1'-Hydroxyimino)-ethyl-4-(3'-tert.-butylamino-2'-hydroxy)-propoxy]-phenyl-N'-methyl-N'-cyclohexylurea, melting point of the fumarate: 166° to 168°C.

34. 3-Acetyl-4-(3'-tert.-butylamino-2'-hydroxy)-propoxyaniline (melting point 115° to 117°C) is dissolved in ethanol and an aqueous solution of hydroxylamine hydrochloride is added. After 20 hours' reaction at room temperature, the 3-(1'-hydroxyimino)-ethyl-4-(3'-tert.-butylamino-2'-hydroxy)-propoxyaniline is isolated in an analogous manner to that used in Example 1 and reacted with dimethylcarbamic acid chloride in pyridine at room temperature. The reaction mixture is concentrated in vacuo, the residue is taken up in water and the aqueous phase is extracted with ethyl acetate. The ethyl acetate phase is separated off, dried and evaporated in vacuo. The residue thus obtained crystallises after trituration with ether. This gives crude N-[3(1'-hydroxyimino)ethyl-4-(3'-tert.-butylamino-2'-hydroxy)-propoxy]-phenyl-N'-dimethylurea which may be converted, in accordance with the procedure described in Example 1, into the fumurate of melting point 210° to 212°C.

What we claim is:

1. A phenoxypropylamine derivatives selected from the group consisting of compounds of the formula:

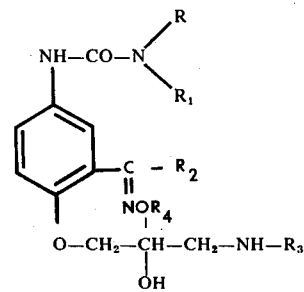

wherein one or both of R and $R_1$ are hydrogen or lower alkyl $R_2$ is hydrogen or lower alkyl, $R_3$ is tertiary butyl or isopropyl and $R_4$ is hydrogen, alkyl containing from 1 to 6 carbon atoms or benzyl, and pharmaceutically acceptable salts thereof.

2. A compound according to claim 1, in which the group

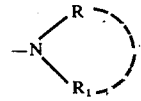

in formula I is lower dialkylamino, $R_2$ is hydrogen, $R_3$ is selected from the group consisting of tertiary butyl and isopropyl and $R_4$ is hydrogen.

3. A compound according to claim 1, N-[3-(1'-Hydroxyimino)-ethyl-4-(3'-tert.-butylamino-2'-hydroxy)-propoxy]-phenyl-n'-dimethylurea.

4. A compound according to claim 1, N-[3-(1'-hydroxyimino)-ethyl-4-(3'-tert.-butylamino-2'-hydroxy)-propoxy]-phenyl-N'-diethylurea.

5. A compound according to claim 1, N-[3-(1'-Hydroxyimino)-ethyl-4-(3'-tert.-butylamino-2'-hydroxy)-prpoxy]-phenyl-N'-methyl-N'-butylurea fumarate.

6. A compound according to claim 1, N-[3-(1'-Hydroxyimino)-methyl-4-(3'-tert.-butylamino-2'-hydroxy)-propoxy]-phenyl-N'-dimethylurea.

7. A compound according to claim 1, N-[3-(1'-Hydroxyimino)-methyl-4-(3'-tert.-butylamino-2'-hydroxy)-propoxy]-phenyl-N'-diethylurea.

* * * * *